(12) United States Patent
Hazlebeck et al.

(10) Patent No.: US 10,597,624 B2
(45) Date of Patent: Mar. 24, 2020

(54) ALGAE CULTIVATION SYSTEMS AND METHODS ADAPTED FOR WEATHER VARIATIONS

(71) Applicant: Global Algae Innovations, Inc., San Diego, CA (US)

(72) Inventors: David A. Hazlebeck, El Cajon, CA (US); Rodney Corpuz, Lihue, HI (US)

(73) Assignee: GLOBAL ALGAE TECHNOLOGIES, LLC, Santee, CA (US)

( * ) Notice: Subject to any disclaimer, the term of this patent is extended or adjusted under 35 U.S.C. 154(b) by 0 days.

(21) Appl. No.: 15/590,430

(22) Filed: May 9, 2017

(65) Prior Publication Data
US 2017/0321179 A1 Nov. 9, 2017

Related U.S. Application Data

(60) Provisional application No. 62/333,721, filed on May 9, 2016.

(51) Int. Cl.
*C12M 1/00* (2006.01)
*C12N 1/12* (2006.01)

(52) U.S. Cl.
CPC ............ *C12M 27/20* (2013.01); *C12M 21/02* (2013.01); *C12M 23/18* (2013.01); *C12N 1/12* (2013.01)

(58) Field of Classification Search
None
See application file for complete search history.

(56) References Cited

U.S. PATENT DOCUMENTS

| | | | |
|---|---|---|---|
| 2,732,662 | A | 1/1956 | Myers et al. |
| 3,243,918 | A | 4/1966 | Machiedo et al. |
| 4,253,271 | A | 3/1981 | Raymond |
| 4,320,594 | A | 3/1982 | Raymond |
| 5,981,271 | A | 11/1999 | Doucha et al. |
| 8,245,440 | B2 | 8/2012 | Ryan et al. |
| 8,318,478 | B2 | 11/2012 | Dahle |

(Continued)

FOREIGN PATENT DOCUMENTS

WO 2013186626 12/2013

OTHER PUBLICATIONS

International Search Report and Written Opinion for related International Patent Application No. PCT/US2017/031689, dated Aug. 16, 2017.
Dodd, "Elements of Pond Design and Construction," CRC Handbook of Microalgal Mass Culture, CRC Press 1986, pp. 265-283.
Chiaramonti et al., "Review of Energy Balance in Raceway Ponds for Microalgae Cultivation: Re-Thinking a Traditional System is Possible," Applied Energy 102, 2013, pp. 101-111.

(Continued)

*Primary Examiner* — David W Berke-Schlessel
(74) *Attorney, Agent, or Firm* — Quarles & Brady LLP

(57) ABSTRACT

Algae cultivation systems and methods account for weather variations that can affect algae cultivation. In one system, an open raceway algae cultivation system includes a channel having a high section and a low liquid collection section. The channel is sloped to allow substantially all of an algae cultivation fluid in the high section to flow downwardly into the low liquid collection section. A barrier is removably positioned in the high section and a drain is positioned in the high section such that, when substantially all of the algae cultivation fluid has collected in the low liquid collection section, any rainwater that falls in the high section flows into the drain, without the rainwater mixing with the algae cultivation fluid in the low liquid collection section.

16 Claims, 9 Drawing Sheets

(56) References Cited

U.S. PATENT DOCUMENTS

| | | | |
|---|---|---|---|
| 8,541,225 B2 | 9/2013 | Hazlebeck et al. | |
| 8,748,162 B2 | 6/2014 | Hazlebeck et al. | |
| 8,752,329 B2 | 6/2014 | Parsheh et al. | |
| 8,769,867 B2 | 7/2014 | Parsheh et al. | |
| 2010/0093078 A1* | 4/2010 | Wang | C12M 21/02 435/325 |
| 2011/0217692 A1 | 9/2011 | Morgan et al. | |
| 2011/0229775 A1 | 9/2011 | Michaels et al. | |
| 2011/0287531 A1 | 11/2011 | Hazlebeck | |
| 2012/0220027 A1 | 8/2012 | Miller, III et al. | |
| 2014/0322805 A1* | 10/2014 | Hazlebeck | C12M 29/12 435/292.1 |
| 2015/0182923 A1 | 7/2015 | Malkiel et al. | |
| 2015/0240197 A1* | 8/2015 | Parsheh | C12M 21/02 435/257.1 |

OTHER PUBLICATIONS

Anderson, Robert A., Algal Culturing Techniques, Elsevier Academic Press 2005. (589 pages).

Bajpai, Rakesh et al. eds., Algal Biorefineries, vol. 1: Cultivation of Cells and Products, Springer 2014. (331 pages).

Das, Debabrata ed., Algal Biorefinery: An Integrated Approach, Springer 2015. (479 pages).

Kumar, et al., Recent trends in the mass cultivation of algae in raceway ponds, 51 Renewable and Sustainable Energy Reviews 875-85 (2015). (11 pages).

Richmond, Open systems for the mass production of photoautotrophic microalgae outdoors: physiological principles, 4 Journal of Applied Phycology 281-86 (1992). (6 pages).

Sahoo, Dinabandhu and Seckbach, Joseph eds., The Algae World, Springer 2015. (594 pages).

* cited by examiner

ALGAE CULTIVATION SYSTEMS AND METHODS ADAPTED FOR WEATHER VARIATIONS

CROSS-REFERENCE TO RELATED APPLICATION(S)

This application claims priority to U.S. provisional application No. 62/333,721, filed on May 9, 2016, which is incorporated by reference herein and relied upon in their entirety.

STATEMENT OF FEDERALLY SPONSORED RESEARCH OR DEVELOPMENT

This invention was made with government support under award #DE-EE0006314 and award #DE-EE0007689, both awarded by the Department of Energy ("DOE"), and under sub-recipient #06-S140633 of prime award #W911NF-14-2-0017 awarded by the Defense Advanced Research Projects Agency ("DARPA"). The government has certain rights in the invention.

BACKGROUND OF THE DISCLOSURE

The present disclosure relates generally to algae cultivation systems and methods, and more particularly to open raceway algae cultivation systems and methods.

Algae cultivation has become widely recognized as a promising source of food, biofuel, chemicals, and nutraceuticals. Typical algae cultivation systems include open raceways for economical production. Short-term weather variations can cause very significant algae cultivation issues in these open raceway systems. For example, algae culture health can be significantly degraded by (i) dilution due to high rainfall events, (ii) overheating due to higher than expected temperatures combined with reduced evaporation from lower wind speeds or higher humidity, and (iii) over cooling due to lower than expected temperatures.

New and improved algae cultivation systems and methods are accordingly needed.

SUMMARY OF THE DISCLOSURE

In one aspect of the present disclosure, an open raceway algae cultivation system includes a channel having a high section and a low liquid collection section. The channel is sloped to allow substantially all of an algae cultivation fluid in the high section to flow downwardly into the low liquid collection section. The system further includes a drain positioned in the high section, and a barrier is removably positioned in the high section such that when substantially all of the algae cultivation fluid has flown into the low liquid collection section, any rainwater that falls in the high section will flow downwardly into the drain, without the rainwater mixing with the algae cultivation fluid in the low liquid collection section.

In another aspect, an open raceway algae cultivation system includes a channel having a high section and low liquid collection section. The channel is sloped to allow substantially all of an algae cultivation fluid in the high section to flow downwardly into the low liquid collection section. The system further includes a gutter defined in the high section, and a drain fluidly coupled to the gutter such that when substantially all of the algae cultivation fluid has flown into the low liquid collection section, any rainwater that falls in the high section will flow downwardly through the gutter into the drain, without the rainwater mixing with the algae cultivation fluid in the low liquid collection section.

In still another aspect, an open raceway algae cultivation system includes a channel configured to contain an algae cultivation fluid during a first time period within a first area and a first depth. The system further includes at least one removable wall positioned inside the channel to contain the algae cultivation fluid during a second time period to a second area and a second depth, the second area less than the first area and the second depth greater than the first depth.

In yet another aspect, a method of removing rainwater from an open raceway algae cultivation system includes circulating an algae cultivation fluid through a sloped channel and stopping the circulation of the fluid through the sloped channel. After the circulation is stopped substantially all of the algae cultivation fluid in the sloped channel is allowed to flow from a high section to a low liquid collection section of the sloped channel. After the algae fluid flows and collects in the liquid collection section, a removable barrier is positioned or placed in the high section of the channel and rainwater is allowed to fall in the high section of the channel to flow (a) towards the removable barrier and (b) into a drain positioned in the high section of the sloped channel.

In another aspect, a method of removing rainwater from an open raceway algae cultivation system includes circulating an algae cultivation fluid through a sloped channel and stopping the circulation of the fluid. After stopping the circulation, substantially all of the algae cultivation fluid in the sloped channel is allowed to flow from a high section of the sloped channel to a low liquid collection section of the channel. After all of the fluid has collected in the low section, any rainwater that falls in the high section of the sloped channel is allowed to flow into a gutter defined in the high section and into a drain fluidly coupled to the gutter.

In another aspect, a method of controlling temperature in an open raceway algae cultivation system includes circulating an algae cultivation fluid in a channel having a first area and a first depth. A removable barrier is positioned in the channel to confine the algae cultivation fluid to a second area and a second depth, the second area smaller than the first area and the second depth greater than the first depth. The removable barrier is removed from the channel to enable the algae cultivation fluid to fill the channel having the first area and the first depth.

It is accordingly one objective of the present disclosure to prevent over dilution of algae culture media in open raceway algae cultivation systems during high rainfall events.

It is a further objective to accommodate or adjust for short-term extreme temperature variations without requiring a large change in culture volume through an entire algae cultivation facility.

DETAILED DESCRIPTION

Figure 1:
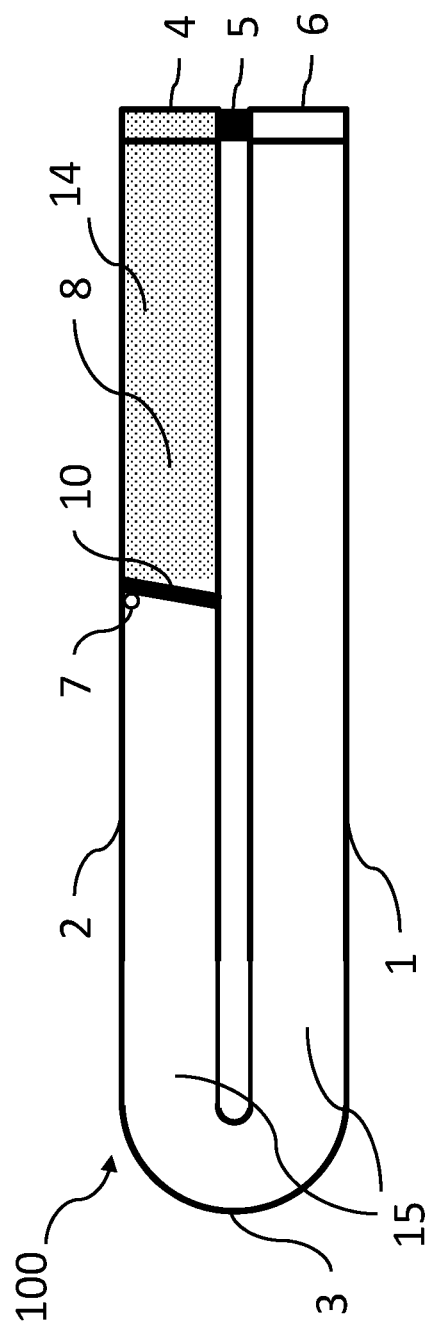
FIG. 1 is a plan view illustrating an open raceway algae cultivation system having a removable barrier according to one embodiment of the present disclosure.

Referring now to the figures, FIG. 1 illustrates an open raceway algae cultivation system having a removable barrier according to one non-limiting embodiment of the present disclosure. The system includes a channel 100 having an upper conduit 1 and a lower conduit 2 fluidly connected via a bend 3 located at one end of the channel 100 or system. Located at the other end of the channel 100 or system is a lower sump 4 fluidly coupled to an upper sump 6 via a pump 5. The lower sump 4 is fluidly coupled to an exit of the lower conduit 2, and the upper sump 6 is fluidly coupled to an entrance of the upper conduit 1. An algae cultivation fluid or slurry 8 is contained in a low liquid collection section 14 of the channel 100 in FIG. 1, as illustrated by the shading in the low liquid collection section 14. A high section 15 of the channel 100 does not contain any algae cultivation fluid 8 in FIG. 1, as illustrated by the lack of shading in the high section 15. The system further includes a removable barrier 10 located in the high section 15 of the channel 100, and a drain 7 located in the high section 15 of the channel 100 for removing rainwater, as discussed below. The removable barrier 10 in certain embodiments is located at a position that is a dividing point or a separator between the high section 15 and the low liquid collection section 14. In certain embodiments, the drain 7 is positioned upstream of the barrier 10.

During normal operation of the system of FIG. 1, the barrier is removed from the channel 100 and the algae cultivation fluid 8 is circulated through the channel 100, including the upper conduit 1 and the lower conduit 2, as well as high section 15 and low section 14. The algae cultivation fluid 8 circulates by exiting the lower conduit 2 and collecting in the lower sump 4. The pump 5 lifts the algae cultivation fluid 8 from the lower sump 4 to the upper sump 6. The upper sump 6 then distributes the algae cultivation fluid 8 to the entrance of upper conduit 1. The bottom of upper conduit 1 is sloped downwardly from the upper sump 6 to the bend 3, and the bottom of the bend 3 is sloped downwardly from the upper conduit 1 to the lower conduit 2. The bottom of lower conduit 2 is sloped downwardly from the bend 3 to the lower sump 4. Thus, the channel 100 is sloped such that during circulation of the fluid 8 or normal operation, the algae cultivation fluid 8 flows by gravity from the upper sump 6 through the upper conduit 1, through the bend 3, through the lower conduit 2, to the lower sump 4. The drain 7 is closed during the normal operation.

The normal operation of the system of FIG. 1 can be discontinued so that the fluid 8 stops circulating through channel 100, and instead collects in the low liquid collection section 14. To discontinue normal operation, the operation of pump 5 is stopped or deactivated. When the pump 5 is stopped, the channel 100 is sloped such that all or substantially all of the algae cultivation fluid 8 flows via gravity from the high section 15 to the low liquid collection section 14, which can include the lower sump 4. Thus, the high section 15 of channel 100, which includes the upper conduit 1, the bend 3 and a portion of the lower conduit 2, will no longer contain the algae cultivation fluid 8 (i.e., the high section 15 becomes substantially empty, as illustrated by the non-shading of section 15 in FIG. 1). Once the fluid has collected in low liquid collection section 14, the removable barrier 8 can be positioned in the high section 15 of channel 100, and the drain 7 can be opened. In one embodiment, the barrier 8 is placed or positioned in a location of the channel 100 that divides the high section 15 from the low section 14, or the fluid 8 collected in the low liquid collection section 14 from the high section 15. The removable barrier 10 acts to prevent any rain that falls in the high or empty section 15 of channel 100 from mixing with the algae cultivation fluid 8 and thereby degrading the fluid 8 for algae cultivation. In other words, any rain that falls in the high section 15 of channel 100 will flow via gravity down the upper conduit 1, around the bend 3 and down the lower conduit 2, into the barrier 10, which acts to divert the rain into the open drain 7. Thus, any rainwater that falls in the high section 15 can be removed from the channel 100 through the open drain 7, without the rainwater mixing with the algae cultivation fluid 8 held in the low liquid collection section 14. It should be appreciated that the removably positionable barrier 10 can be any structure suitable for diverting rainwater in channel 100. In one embodiment, barrier 10 includes a wall that is placed in the high section 15 or lower conduit 2 of channel 100. To prevent mixing of rainwater with fluid 8, the wall can have a weight sufficient to remain in place against the force of any rainwater that flows against one side of wall or any algae fluid 8 that may be contacting the other side of the wall, and a width substantially the same as the width of the lower conduit 2. In another embodiment, the wall can be inserted into slots defined in the sidewalls of the lower conduit 2. In other embodiments, the barrier 100 includes a flexible tube, or an inflatable bladder as discussed in more detail below.

Figure 2:
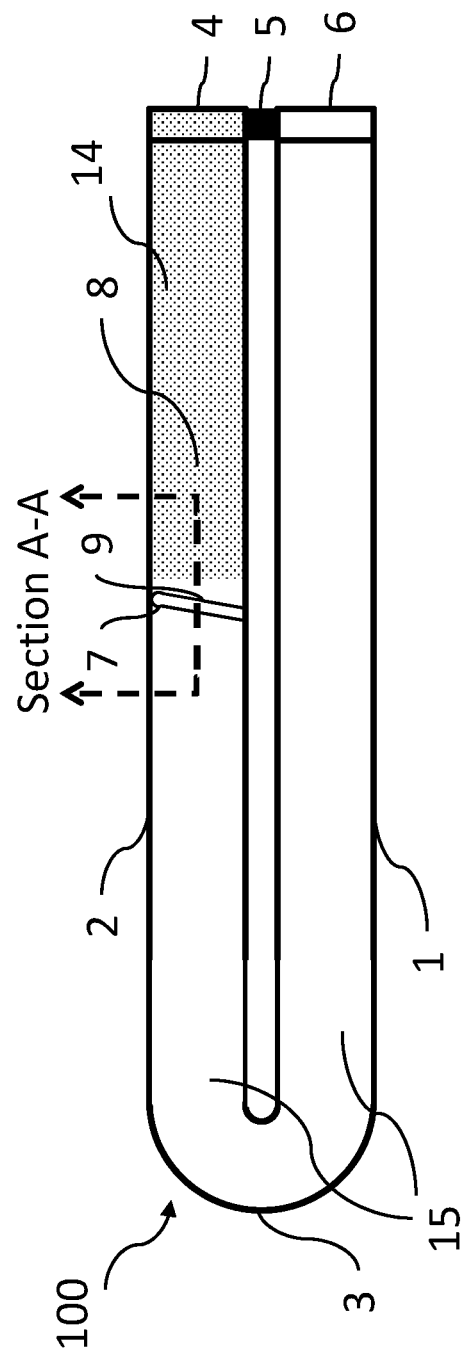
FIG. 2 is a plan view illustrating an open raceway algae cultivation system having a gutter according to one embodiment of the present disclosure.
Figure 3:
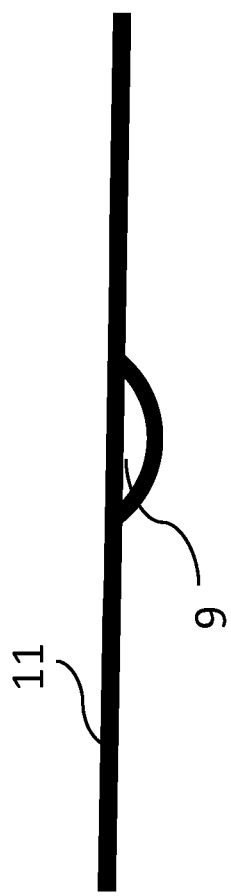
FIG. 3 is a cross-sectional view taken along lines A-A of FIG. 2.

Turing now to FIGS. 2 and 3, FIGS. 2 and 3 illustrate an open raceway algae cultivation system having a gutter according to another non-limiting embodiment of the present disclosure. FIG. 2 is a plan view, while FIG. 3 is a cross-sectional view taken along lines A-A of FIG. 2. The system of FIGS. 2 and 3 include many of the same components described above in connection with the system of FIG. 1. Those components in FIGS. 2 and 3 are marked with the same element numbers used in FIG. 1. The description of those elements, including each of the alternatives discussed above in connection with FIG. 1 apply in many respects to like element numbers in FIGS. 2 and 3.

In particular, the open raceway algae cultivation system of FIGS. 2 and 3 includes a channel 100 having an upper conduit 1 and a lower conduit 2 fluidly connected via a bend 3 located at one end of the channel 100 or system. Located at the other end of the channel 100 or system, is a lower sump 4 which is fluidly coupled to an upper sump 6 via a pump 5. The lower sump 4 is fluidly coupled to an exit of the lower conduit 2, and the upper sump 6 is fluidly coupled to an entrance of the upper conduit 2. An algae cultivation fluid or slurry 8 is located in a low liquid collection section 14 of the channel 100, as illustrated by the shading in the low liquid collection section 14. A high section 15 of channel 100 does not include any algae cultivation fluid 8, as illustrated by the lack of shading in the high section of the channel 10.

The system of FIGS. 2 and 3 differs from the system of FIG. 1 in that the system of FIGS. 2 and 3 includes a gutter 9 defined in a bottom 11 of the high section 15 of channel 100, and a drain 7 that is connected to or coupled fluidly to the gutter 9 in the high section 15. The gutter 9 in certain embodiments is positioned in channel 100 at a position that is a dividing point or a separator between high section 15 and the low liquid collection section 14, or between high section 15 and the fluid 8 collected in section 14. Like the system of FIG. 1, during normal operation of the system of FIGS. 2 and 3, algae cultivation fluid 8 is circulated through the channel 100, including the upper conduit 1 and the lower conduit 2 (as well as high section 15 and the low section 14). The algae cultivation fluid 8 circulates by exiting the lower conduit 2 and collecting in lower sump 4. The pump 5 lifts the algae cultivation fluid 8 from the lower sump 4 to the upper sump 6. The upper sump 6 then distributes the algae cultivation fluid 8 into an entrance of the upper conduit 1. The bottom of upper conduit 1 is sloped downwardly from the upper sump 6 to the bend 3, and the bottom of the bend 3 is sloped downwardly from the upper conduit 1 to the lower conduit 2. The bottom of the lower conduit 2 is sloped downwardly from the bend 3 to the lower sump 4. Thus, the channel 100 of the system of FIGS. 2 and 3 is sloped such that during circulation or normal operation, the algae cultivation fluid 8 flows by gravity from the upper sump 6 through the upper conduit 1, through the bend 3, through the lower conduit 2, to the lower sump 4. The drain 7 is closed during the normal operation while the fluid 8 circulates in the channel 100. The gutter 9 is sized so that the fluid 8 flows over the gutter 9 during normal operation.

Like the system of FIG. 1, the normal operation of the system of FIGS. 2 and 3 can be discontinued or stopped so that the fluid 8 stops circulating through channel 100, and instead collects in the low liquid collection section 14. To discontinue normal operation, the operation of pump 5 is stopped or deactivated. When the pump 5 is stopped, the channel 100 is sloped such that all or substantially all of the algae cultivation fluid 8 flows via gravity from the high section 15 to the low liquid collection section 14, which can include the lower sump 4. Thus, the high section 15 of channel 100, which includes the upper conduit 1, the bend 3 and a portion of the lower conduit 2, will no longer contain the algae cultivation fluid 8 (i.e., the high section 15 becomes substantially empty, as illustrated by the non-shading of section 15 in FIG. 2). In other words, fluid 8 flows from the high or empty section 15 of channel 100 down the upper conduit 1, around the bend 3 and down the lower conduit 2, until the fluid 8 enters into gutter 9, which acts to divert the rain into the open drain 7. Thus, any rainwater that falls in high section 15 is removed through open drain 7, without mixing with the fluid 8. Rainwater does not flow over the gutter 9 because the rainwater is continuously being removed via the drain 7, so the level of rainwater does not increase high enough to overflow the drain 7. In an embodiment, the portion of the bottom 11 of the channel illustrated in FIG. 3 can be relatively flat with a 1° slope downward from left to right. The gutter 9 can be an indentation in the bottom 11 as illustrated, or any other suitable form or shape that allows the rainwater to be diverted into drain 7.

Figure 4:
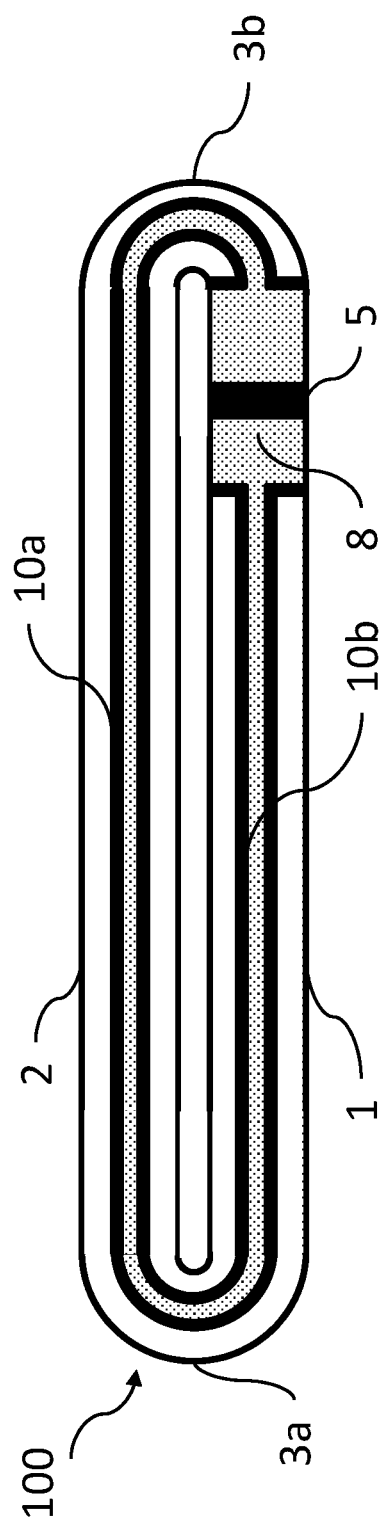
FIG. 4 is a plan view illustrating an open raceway algae cultivation system having removable walls according to one embodiment of the present disclosure.

FIG. 4 is a plan view illustrating an open raceway algae cultivation system having at least one removable wall for temporarily reducing an area and depth of the channel 100 according to another embodiment of the present disclosure. The system of FIG. 4 includes many of the same components described above in connection with the system of FIG. 1. Those components in FIG. 4 are marked with the same or similar element numbers as FIG. 1. The description of those elements including each of the alternatives discussed above in connection with FIG. 1 apply in many respects to like element numbers in FIG. 4.

In particular, the system of FIG. 4 includes a channel 100 having an upper conduit 1 and a lower conduit 2. Here, however, the system of FIG. 4 includes first and second bends 3a, 3b, and a pump 5 that lifts the algae cultivation fluid 8 from the lower conduit 2 to the upper conduit 1. The bottom of upper conduit 1 is sloped downwardly from the pump 5 to the first bend 3a. The bottom of first bend 3a is sloped downwardly from the upper conduit 1 to the lower conduit 2. The bottom of lower conduit 2 is sloped downwardly from the first bend 3a to the second bend 3b, and the bottom of the second bend 3b is sloped downwardly from the lower conduit 2 to the pump 5.

As illustrated in FIG. 4, at least one removable sidewall 10a, 10b has been positioned or placed inside the channel 100 to confine the algae cultivation fluid 8 to a reduced area and increased depth of channel 100. In one embodiment, as illustrated in FIG. 4, the at least one sidewall 10a, 10b includes an outer sidewall 10a and an inner sidewall 10b, which together form a shape that is similar to the shape defined by channel 100 (e.g., an oval like shape). The inner and outer walls 10a, 10b define an area for containing the fluid 8 that is less than the area of channel 100 and a depth that is greater than the depth of the channel 100 without the sidewalls 10a, 10b.

FIG. 4 illustrates the system during a time in which the sidewalls 10a, 10b have been placed in the channel 100, and the algae cultivation fluid 8 is contained within the sidewalls 10a, 10b at an increased depth and decreased area. While the algae cultivation fluid 8 is shown as being contained within sidewalls 10a, 10b, it should be appreciated that when the walls 10a, 10b are removed from the channel 100, the algae cultivation fluid 8 is contained within the walls defined by the channel 100. In other words, when the walls 10a, 10b are removed or not positioned in the channel 100, the channel 100 contains the algae cultivation fluid 8 during a first time period having a first area and a first height, and when the walls 10a, 10b are placed in the channel 8 during a second time period, the fluid 8 is contained within a second area that is less than the first area, and contained within a second height that is greater than the first height. In either time period or condition, the system of FIG. 4 operates by the pump 5 lifting the algae cultivation fluid or slurry 8 to the height of the upper conduit 1, where the fluid 8 flows by gravity from the pump 5 through the upper conduit 1, around the first bend 3a, through the lower conduit 2, around the second bend 3b, and back to the inlet of the pump 5. It should be appreciated that the at least one removable wall 10a, 10b can in certain embodiments be a single removable wall that is placed in the channel 100 and, which along with the existing inner or outer wall of channel 100, contains the algae cultivation fluid 8 in a reduced area having an increased depth.

Figure 5:
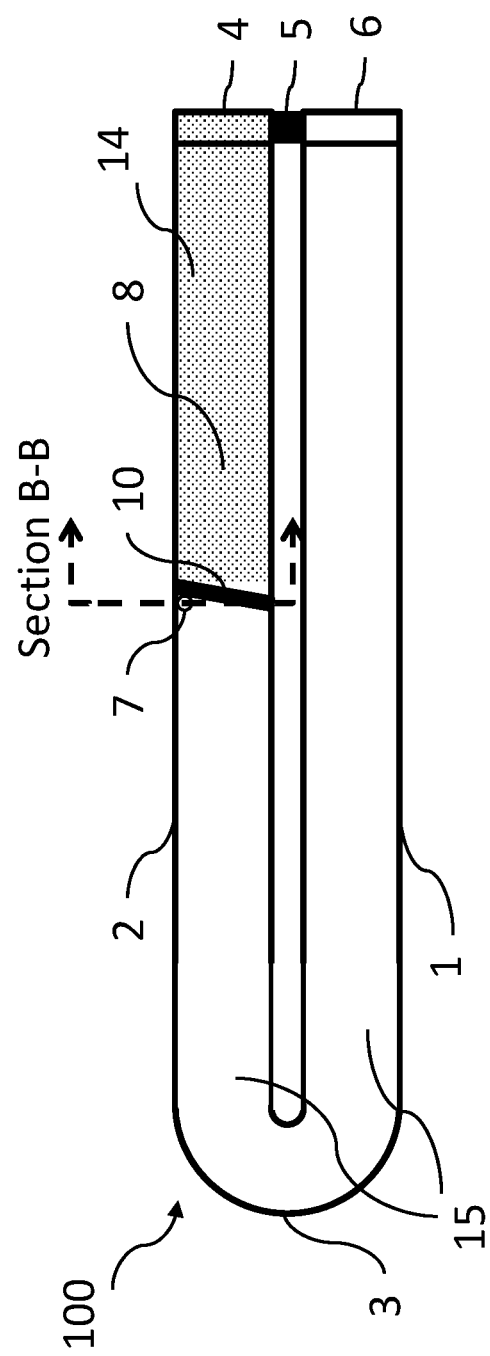
FIG. 5 is a plan view illustrating an open raceway algae cultivation system having a removable barrier in the form of a flexible tube according to one embodiment of the present disclosure.
Figure 6:
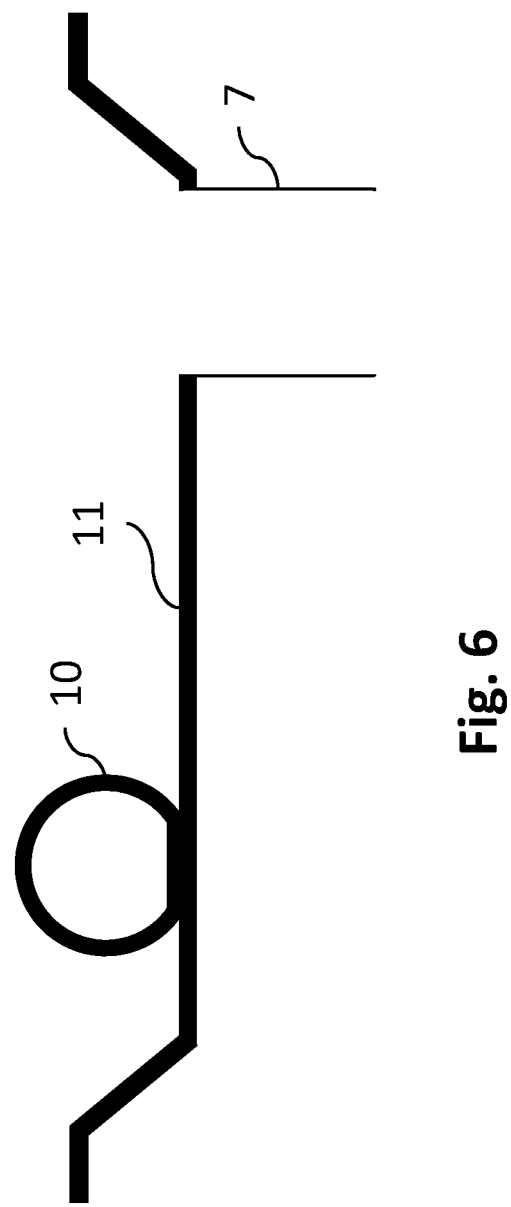
FIG. 6 is a cross-sectional view taken along lines B-B of FIG. 5.

FIGS. 5 and 6 illustrate an open raceway algae cultivation system having a removable barrier in the form of a flexible tube according to another embodiment of the present disclosure. FIG. 5 is a plan view, while FIG. 6 is a cross-sectional view taken along lines B-B of FIG. 5. The system of FIGS. 5 and 6 is similar to the system of FIG. 1, and includes many of the same components described above in connection with the system of FIG. 1. Those components in FIGS. 5 and 6 are marked with the same element numbers used in FIG. 1. The description of those elements including each of the alternatives discussed above in connection with FIG. 1 apply to like element numbers in FIGS. 5 and 6.

The removable barrier in FIGS. 5 and 6 includes a flexible tube 10, which can be lowered into the channel 100. The flexible tube 10 can be placed in the channel 100 manually, or the system can include a mechanism to automatically lift and lower the tube 10 to position the tube 10 in the channel 100. It should be appreciated that the flexible tube 10 of FIGS. 5 and 6 could be used for the at least one sidewall discussed in connection with the system of FIG. 4 above or for the barrier 10 in the system of FIG. 1. In certain embodiments, the flexible tube 10 can be filled or partially filled with water or sand to provide extra weight to hold the tube 10 in place within the channel 100. The drain 7 in the system of FIGS. 5 and 6 can be placed in the bottom 11 of the channel 100 to provide a conduit to remove rainwater.

Figure 7:
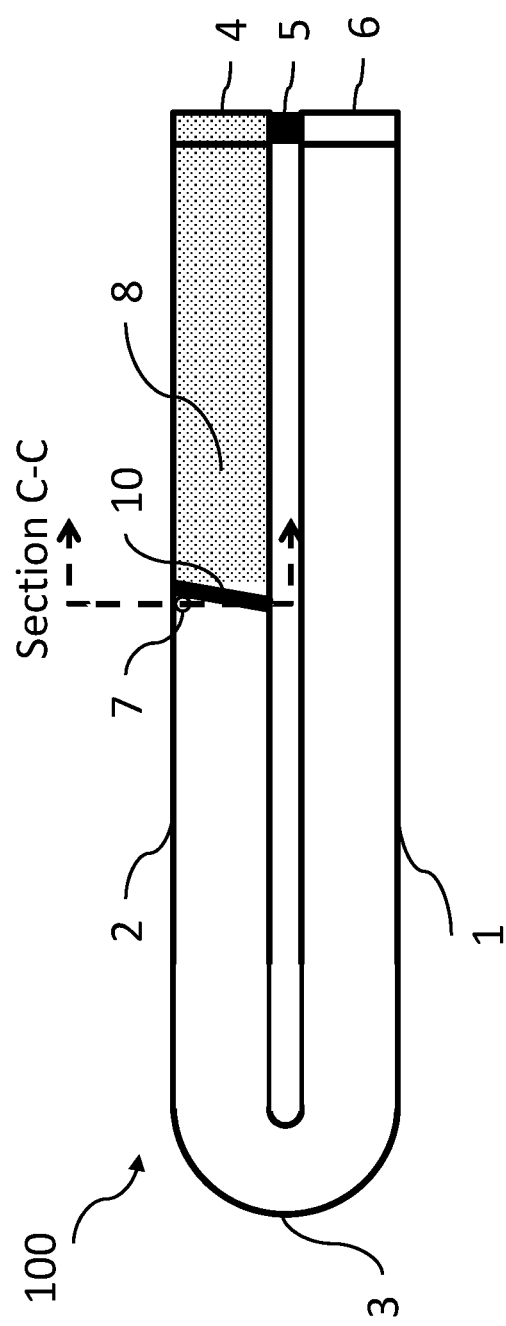
FIG. 7 is a plan view illustrating an open raceway algae cultivation system having a removable barrier or bladder located beneath a liner according to one embodiment of the present disclosure.
Figure 8:
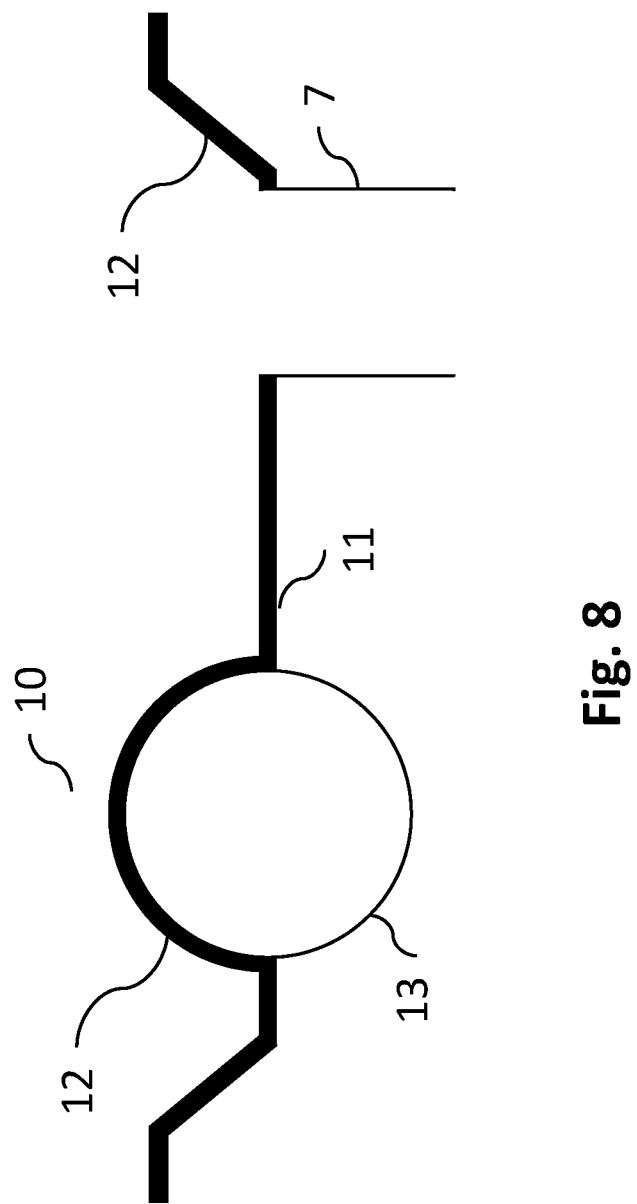
FIG. 8 is a cross-sectional view taken along lines C-C of FIG. 7.

FIGS. 7 and 8 illustrate an open raceway algae cultivation system having a removable barrier or bladder located beneath a liner according to another embodiment of the present disclosure. FIG. 7 is a plan view, while FIG. 8 is a cross-sectional view taken along lines C-C in FIG. 7. The system of FIGS. 7 and 8 is similar to the system of FIG. 1, and includes many of the same components described above in connection with the system of FIG. 1. Those components in FIGS. 7 and 8 are marked with the same element numbers used in FIG. 1. The description of those elements including each of the alternatives discussed above in connection with FIG. 1 apply to like element numbers in FIGS. 7 and 8.

Here, the bottom 11 of channel 100 is covered with a flexible liner 12, and a flexible bladder 13 is located beneath the liner 12. To expand the bladder 13, the bladder 13 can be filled with air or water. Filling the bladder with air or water causes the liner 12 to be raised, creating a barrier 10. In an embodiment, the system of FIGS. 7 and 8 includes a pump to fill the bladder 13 with the air and/or a compressor to fill the bladder 13 with gas. To remove the barrier 10, the water or air can be released or withdrawn from the bladder 13 to allow the liner 12 to fall back into place along the bottom 11 of channel 100. The drain 7 perforates the liner 12 in the bottom 11 of the channel 100 to provide a conduit to remove any rainwater. It should be appreciated that like the tube 10 of FIGS. 5 and 6, the bladder 13 and liner 12 of FIGS. 7 and 8 can likewise be used for the barrier 10 in the system of FIG. 1.

It should be appreciated from the foregoing that a method of removing rainwater from an open raceway algae cultivation system of the present disclosure includes (i) circulating an algae cultivation fluid through a sloped channel; (ii) stopping the circulation of the algae cultivation fluid through the sloped channel; (iii) after (ii), allowing substantially all of the algae cultivation fluid in the sloped channel to flow from a high section of the sloped channel to a low liquid collection section of the sloped channel; (iv) after (iii), positioning a removable barrier in the high section of the sloped channel; and (v) allowing rainwater that falls in the high section of the sloped channel to (a) flow towards the removable barrier and (b) into a drain positioned in the high section of the sloped channel.

Another method of removing rainwater from an open raceway algae cultivation system of the present disclosure includes (i) circulating an algae cultivation fluid through a sloped channel; (ii) stopping circulation of the algae cultivation fluid; (iii) after (ii), allowing substantially all of the algae cultivation fluid in the sloped channel to flow from a high section of the sloped channel to a low liquid collection section of the sloped channel; (iv) after (iii), allowing rainwater that falls in the high section of the sloped channel to (a) flow into a gutter defined in the high section of the sloped channel and (b) into a drain positioned in the gutter. The method can further include removing the algae cultivation fluid that has collected in the gutter prior to (iv).

Figure 9:
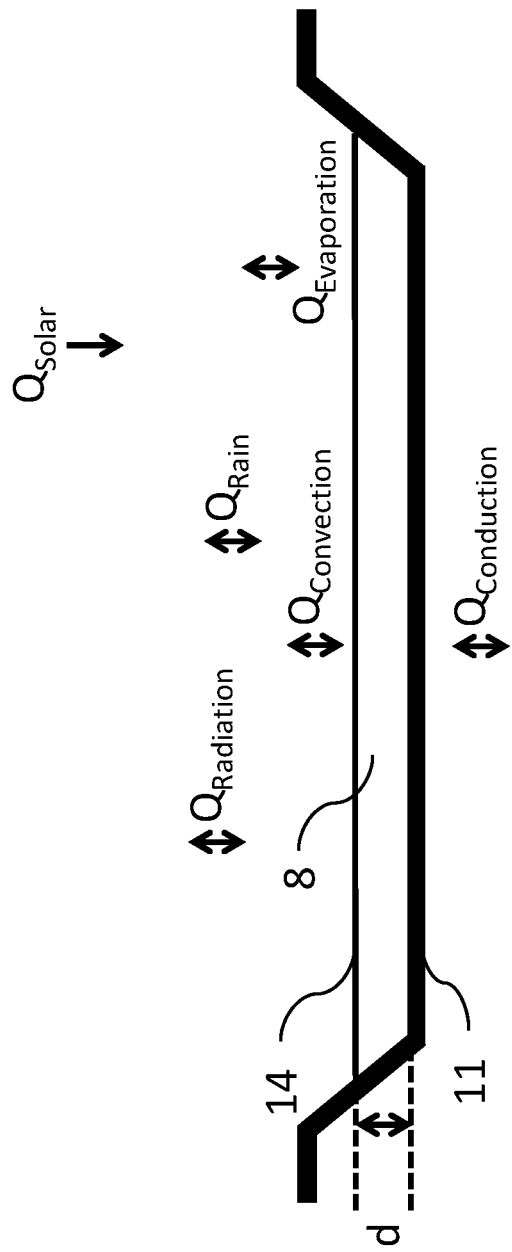
FIG. 9 illustrates heat that can flow into and out of an open raceway algae cultivation system of the present disclosure.

FIG. 9 is a diagram illustrating heat that can flow into or out of any one of the open raceway algae cultivation systems or methods of the present disclosure. In particular, FIG. 9 shows a gas-liquid interface 14 between an algae cultivation fluid 8 and the air. A liquid-solid interface 11 exits between the algae slurry 8 and the ground. The system is cooled by evaporation of water and is heated by condensation of water $Q_{Evaporation}$. During the day, the system is heated by solar radiation $Q_{Solar}$. The system is cooled or heated by convection $Q_{Convection}$ and by radiation $Q_{Radiation}$ to the air depending on whether the algae cultivation fluid 8 is hotter than the air or cooler than the air, respectively. Similarly, the system is cooled or heated by conduction $Q_{Conduction}$ to the ground depending on whether the system is hotter or cooler than the ground, respectively. Similarly, the system is cooled or heated by rain $Q_{Rain}$ depending on whether the rainwater is cooler or hotter than the algae cultivation fluid 8, respectively. The magnitude of each of these heat fluxes is dependent on the area of the raceway, A: Total heat flow=Q×A.

The impact of the heat flow on the temperature of the raceway is proportional to the depth of the system d: $Q \times A \times \Delta t = Cp \times d \times A \times \Delta T$, where Cp is the heat capacity and $\Delta T$ is the change in temperature of the algae cultivation fluid 8 and $\Delta t$ is the time period. Increasing the depth will reduce the change in temperature of the algae cultivation fluid for a given heat flux Q and time period $\Delta t$. Decreasing the depth will increase the change in temperature of the algae cultivation fluid for a given heat flux and time period. In addition to depth, there are other means to control temperature changes to the system, such as adding water that is a cooler or hotter than the algae cultivation fluid, adding or removing a shade or infrared screen above the system, or using an active heat exchanger.

It should be appreciated from the foregoing that a method of controlling temperature in an open raceway algae cultivation system of the present disclosure includes circulating an algae cultivation fluid in a channel having a first area and a first depth; positioning a removable barrier in the channel to confine the algae cultivation fluid to a second area and a second depth, the second area smaller than the first area and the second depth greater than the first depth; removing the removable barrier to enable the algae cultivation fluid to fill the channel having the first area and the first depth. The method can further include said positioning of the removable barrier occurring during one of (i) the daytime, or (ii) the nighttime.

It should additionally be appreciated that each of the embodiments described herein including the methods can operate with one or more controllers, which can be programmed or configured to operate with any of the pumps, compressors, walls, removable barriers, to carry out various functions of the systems or methods including generating the pumping of the fluid, gas or positioning the barriers in the channels. In an embodiment, the one or more controllers can include at least one processor and at least one memory device which stores instructions, which when executed by the at least one processor, cause the at least one processor to operate with one or more of the pumps or removable barriers to perform said operations of the algae cultivation systems and methods. It should additionally be appreciated that certain embodiments can include at least one input device and/or at least one display device, and the one or more controllers can be programmed or configured to operate with the at least at least one input device and/or the at least one display device.

Example 1

The operational depth of a channel raceway is 6 cm. A large rainfall of 4 cm occurs overnight. If the raceway does not have a method of diverting the rain, then the raceway depth will be increased to 10 cm, and the concentration of nutrients, salt, and algae in the raceway will be reduced by 40%. This rapid change in concentration and dilution of the algae can have severe effects on the algae culture health and productivity. If the operational depth is 6 cm for a channel or raceway configured as in FIG. 1, with a 0.1% slope, a 1000 m channel length, and 10% of the culture volume in the sump, then when the circulation pump is stopped the algae cultivation fluid will only fill the sump and 46% of the lower conduit. Thus, about 77% of the raceway or channel will be empty. A rainfall of 4 cm occurs overnight. If a removable of barrier is put in place before the rainfall, and the rainwater falling on the empty portion of the channel or raceway is removed, then the raceway depth will be increased to 6.9 cm and the concentration of nutrients, salt, and algae in the raceway will be reduced by 13%. This change in depth will have a much lower effect on algae culture health and productivity than a raceway without the removable barrier and drain to remove rainwater.

Example 2

A raceway or channel depth of 5 cm provides a night-time algae cultivation fluid low temperature of 20° C. and a day time high temperature of 30° C. under typical weather conditions. The algae has a maximum allowable daytime temperature of 34° C. A change in weather results in abnormally high daytime temperatures and humidity for two days such that a depth of 20 cm would be required to keep the daytime temperature below 34° C. Increasing the depth of the raceway would require shifting to a new operating range with a depth that is much higher than the optimal range once the weather returns to normal. If the raceway or channel is configured as in FIG. 3, then the removable barriers could be put in place to reduce the raceway area during periods where heat is being added to the raceway, which would effectively increase the depth for the two days of abnormally high temperatures. Once the weather returns to the normal range, the barriers could be removed and the optimal operating depth would be restored.

Example 3

A raceway or channel depth of 5 cm provides a nigh-time algae cultivation fluid low temperature of 10° C. and a day time high temperature of 15° C. under typical weather conditions. If the temperature for the algae cultivation fluid is too low then there is a significant reduction in algae productivity. A change in weather results in short-term freezing conditions that would cause too low of temperature so that the algae culture health and productivity is reduced unless the depth is increased. Increasing the depth of the channel or raceway would require shifting to a new operating range with a depth that is much higher than the optimal range once the weather returns to normal. If the raceway is configured as in FIG. 3, then the removable barriers can be in place during the morning and late afternoon when the net heat flux causes the raceway to cool. The barriers can be removed during the mid-day when the temperature and solar radiation is high enough to warm the algae slurry. In this way, the inflow of heat is maximized and the loss of heat is minimized so that the algae culture health and productivity can be maintained without shifting the raceway to a new operating range by adding culture media.

What is claimed is:

1. An open raceway algae cultivation system comprising:
    a channel including a high section and a low liquid collection section, the channel sloped to allow substantially all of an algae cultivation fluid in the high section to flow downwardly into the low liquid collection section;
    a drain positioned in the high section; and
    a barrier removably positioned in the high section,
    wherein the system has a first configuration in which the drain is closed and the barrier is removed,
    wherein the system has a second configuration in which the drain is open and the barrier is positioned so as to prevent fluid flow from the high section to the low liquid collection section, and
    wherein the system is configured to convert from the first configuration to the second configuration after substantially all of the algae cultivation fluid has flown into the low liquid collection section, such that any rainwater that falls in the high section in the second configuration will flow downwardly into the drain, without the rainwater mixing with the algae cultivation fluid in the low liquid collection section.

2. The open raceway algae cultivation system of claim 1, wherein the barrier includes a flexible tube configured to be lowered into the channel.

3. The open raceway algae cultivation system of claim 2, wherein the flexible tube is filled with at least one of water or sand to hold the flexible tube in place in the first section of the channel.

4. The open raceway algae cultivation system of claim 1, which includes an algae cultivation fluid circulator configured to, when the barrier has been removed from the position in the channel and the drain has been closed, circulate the algae cultivation fluid through the channel including the high section and the low liquid collection section.

5. The open raceway algae cultivation system of claim 1, wherein the channel includes a bottom, and wherein the barrier includes (i) a flexible liner covering the bottom of the channel, and (ii) an inflatable bladder positioned under the flexible liner.

6. The open raceway algae cultivation system of claim 5, which includes one of (i) a pump configured to fill the inflatable bladder with liquid, or (ii) a compressor configured to fill the inflatable bladder with gas.

7. The open raceway algae cultivation system of claim 1, which includes (i) an upper sump, and (ii) a lower sump positioned at one end of the channel, and wherein the low liquid collection section includes the lower sump.

8. The open raceway algae cultivation system of claim 1,
    wherein the channel includes (i) a lower conduit, (ii) an upper conduit, and (iii) a bend coupling fluidly the lower conduit to the upper conduit;
    which includes (a) a lower sump positioned at an exit of the lower conduit; (b) an upper sump positioned at an entrance of the upper conduit; and (c) and a pump configured to lift the algae cultivation fluid in the lower sump to the upper sump such that the upper sump can deliver the algae cultivation fluid to the entrance of the upper conduit and the algae cultivation fluid can flow from the upper conduit to the lower conduit; and wherein the low liquid collection section of the channel includes the lower sump.

9. An open raceway algae cultivation system comprising:
a channel including a high section and low liquid collection section, the channel sloped to allow substantially all of an algae cultivation fluid in the high section to flow downwardly into the low liquid collection section;
a gutter defined in the high section; and
a drain fluidly coupled to the gutter,
wherein the system has a first configuration in which the drain is closed so as to permit substantially all of the algae cultivation fluid to flow into the low liquid collection section,
wherein the system has a second configuration in which the drain is open, and
wherein the system is configured to convert from the first configuration to the second configuration after substantially all of the algae cultivation fluid has flown into the low liquid collection section, such that any rainwater that falls in the high section will flow downwardly through the gutter into the drain, without the rainwater mixing with the algae cultivation fluid in the low liquid collection section.

10. The open raceway algae cultivation system of claim 9, which includes an algae cultivation fluid circulator configured to (i) circulate the algae cultivation fluid through the channel including the high section and the low liquid collection section, and (ii) stop circulating the algae cultivation fluid through the channel to allow (a) substantially all of the algae cultivation fluid to flow downwardly to the low liquid collection section and (b) any rainwater that falls in the high section to flow downwardly through the gutter into the drain.

11. An open raceway algae cultivation system comprising:
a channel configured to contain an algae cultivation fluid during a first time period within a first area and a first depth; and
at least one removable wall positioned inside the channel to contain the algae cultivation fluid during a second time period to a second area and a second depth, the second area less than the first area and the second depth greater than the first depth, the removable wall configured to prevent fluid other than the algae cultivation fluid from flowing from the first area to the second area.

12. The open raceway cultivation system of claim 11, wherein the at least one removable wall includes at least one flexible tube, and wherein the system is configured to be lowered inside the channel.

13. The open raceway cultivation system of claim 12, wherein the at least one flexible tube is configured to be filled with one of (i) water or (ii) sand.

14. The open raceway cultivation system of claim 11, wherein (i) the at least one removable wall includes an inner wall and an outer wall, and (ii) the algae cultivation fluid is confined between the inner and outer walls during the second time period.

15. The open raceway cultivation system of claim 11, wherein (i) the channel includes a bottom, and (ii) the at least one removable wall includes a (a) a flexible liner covering the bottom of the channel, and (b) an inflatable bladder located under the flexible liner.

16. The cultivation system of claim 15, which includes one of (i) a pump configured to fill the inflatable bladder with liquid, or (ii) a compressor configured to fill the inflatable bladder with gas.

* * * * *